United States Patent
Pelletier et al.

(12) 
(10) Patent No.: US 6,378,364 B1
(45) Date of Patent: Apr. 30, 2002

(54) DOWNHOLE DENSITOMETER

(75) Inventors: Michael T. Pelletier, Houston; Mark A. Proett, Missouri City; Bruce H. Storm, Jr., Houston; James Robert Birchak, Spring; Thomas Edward Ritter, Katy, all of TX (US)

(73) Assignee: Halliburton Energy Services, Inc., Dallas, TX (US)

( * ) Notice: Subject to any disclaimer, the term of this patent is extended or adjusted under 35 U.S.C. 154(b) by 0 days.

(21) Appl. No.: 09/482,793

(22) Filed: Jan. 13, 2000

(51) Int. Cl.$^7$ .............................. E21B 44/00; G01F 1/84
(52) U.S. Cl. .................................. 73/152.47; 73/861.355
(58) Field of Search ...................... 73/861.355, 861.356, 73/861.357, 152.47

(56) References Cited

U.S. PATENT DOCUMENTS

| | | | |
|---|---|---|---|
| 4,823,614 A | * 4/1989 | Dahlin .................... | 73/861.357 |
| 5,005,400 A | 4/1991 | Lew ........................ | 73/32 |
| 5,009,109 A | * 4/1991 | Kalotay et al. .......... | 73/861.356 |
| 5,048,349 A | 9/1991 | Wolff ...................... | 73/861.37 |
| 5,331,859 A | * 7/1994 | Zolock ................... | 73/861.356 |
| 5,351,561 A | * 10/1994 | Wenger et al. .......... | 73/861.357 |
| 5,363,706 A | * 11/1994 | Lew ........................ | 73/861.355 |
| 5,796,012 A | * 8/1998 | Gomi et al. ............. | 73/861.357 |
| 5,827,979 A | * 10/1998 | Schott et al. ........... | 73/861.357 |

FOREIGN PATENT DOCUMENTS

AU 551888 5/1986

OTHER PUBLICATIONS

*Measurements& Control News*, Sep. 1993, vol. 27, No. 4 Issue 160 12 pp.
*Mass Flowmeters*, Flow Measurement, Copyright © Copyright Instrument Society of America 1991, pp. 221–247.

*Straight–Tube Mass Flow and Density Meters*, Micro Motion T–Series, Product Data Sheet, PS–00371, Jun. 1999, 8 pp.

* cited by examiner

*Primary Examiner*—Hezron Williams
*Assistant Examiner*—Jay L. Politzer
(74) *Attorney, Agent, or Firm*—William M. Imwalle; Daniel J. Krueger

(57) ABSTRACT

A measurement device is provided that determines fluid properties from vibration frequencies of a sample cavity and a reference cavity. In one embodiment, the measurement device includes a sample flow tube, a reference flow tube, vibration sources and detectors mounted on the tubes, and a measurement module. The sample flow tube receives a flow of sample fluid for characterization. The reference flow tube is filled with a reference fluid having well-characterized properties. The measurement module employs the vibration sources to generate vibrations in both tubes. The measurement module combines the signals from the vibration detectors on the tubes to determine properties of the sample fluid, such as density, viscosity, compressibility, water fraction, and bubble size. The measurement module may further detect certain flow patterns such as slug flow, for example. To measure the sample fluid density, the measurement module determines the difference between resonance frequencies of the sample flow tube and the reference flow tube. The density can then be calculated according to a formula. Other fluid properties may be determined from the sample tube's resonance peak amplitude, peak width and/or peak shape. Variation of the density measurements may be used to detect and characterize multiple phase fluid flow. The use of a reference tube in the disclosed measurement device is expected to greatly enhance the accuracy and reliability of the measurement device over a range of temperatures, pressures, and shock accelerations such as those that may be found downhole in a well.

38 Claims, 5 Drawing Sheets

DOWNHOLE DENSITOMETER

BACKGROUND OF THE INVENTION

1. Field of the Invention

The present invention generally relates to devices and methods for measuring fluid density and other fluid flow properties in a flow stream, where fluid is taken to mean any liquid, gas, or mixture thereof, including those which contain solids. More particularly, the present invention relates to a high accuracy density and viscosity measurement device suitable for use in a high-temperature, high-pressure, high-shock environment such as may be encountered in a wellbore.

2. Description of the Related Art

There are many instances in industrial processes and controls for handling flowing fluids where the density of the moving fluid has to be determined accurately. One particular application is in the identification of reservoir fluids flowing in a well. Water often co-exists with crude oil in some common geologic formations. As such, both substances are often pumped up together by a working oil well and the water is ultimately separated from the crude oil at a downstream location. It is desirable to determine the amount of oil that occurs in an oil-water stream flowing from a formation. To accurately determine the amount of crude oil extracted from a formation, a "net oil computer" may be used to ascertain the amount of crude oil. The "net oil computer" determines the total volume flow rate of the flow stream and calculates the flow stream's oil percentage (based on density measurements) to determine the net amount of oil that emanates from the formation. Given the large quantities of crude oil that are usually involved, any small inaccuracies in measuring density can disadvantageously accumulate over a relatively short interval of time to become a large error in a totalized volumetric measure.

Another particular application of density measurement is to determine the mass flow rate of a fluid medium. Mass flow rate can be calculated as a product of a fluid density (determined by a density meter) and a volume flow rate of the fluid (measured by a volumetric flowmeter). There are mass flowmeters available at the present time such as the Coriolis force or convective inertia force mass flowmeters and thermal probe mass flowmeters. These types of mass flowmeters, while they function excellently in the mass flow measurement of low viscosity fluids, work poorly in measuring flows of highly viscous fluids. The fluid's viscosity introduces error in the data acquisition for the mass flow rate. One of the more promising approaches to measurement of the mass flow rate is to combine an accurate density meter and a reliable positive displacement volumetric flowmeter. This combination is particularly effective in measuring mass flow rates of highly viscous fluids or mixtures of fluids and gasses.

Coriolis mass flow meters can be used to measure the density of an unknown process fluid. In general, as taught, for example, in U.S. Pat. No. 4,491,025, a Coriolis meter can contain two parallel conduits, each typically being a U-shaped flow tube. Each flow tube is driven such that it oscillates about an axis. As the process fluid flows through each oscillating flow tube, movement of the fluid produces reactionary Coriolis forces that are perpendicularly oriented to the plane of the fluid's angular velocity in the tube. These reactionary Coriolis forces cause each tube to twist about a torsional axis that, for U-shaped flow tubes, is normal to its bending axis. The net effect is a slight deformation and deflection of the conduit proportional to the mass flow rate of the fluid. This deformation is normally measured as a small difference between the deflection at the inlet ends of the conduits compared to the deflection at the outlet ends. Both tubes are oppositely driven such that each tube behaves as a separate tine of a tuning fork and thereby advantageously cancels any undesirable vibrations that might otherwise mask the Coriolis forces. The resonant frequency at which each flow tube oscillates depends upon its total mass, i.e. the mass of the empty tube itself plus the mass of the fluid flowing therethrough. Inasmuch as the total mass will vary as the density of the fluid flowing through the tube varies, the resonant frequency will likewise vary with any changes in density.

As specifically taught in U.S. Pat. No. 4,491,009, the density of an unknown fluid flowing through an oscillating flow tube is proportional to the square of the period at which the tube resonates. While the circuit taught in this patent may provide accurate density measurements, it unfortunately possesses several drawbacks. First, for certain application, density measurements to an accuracy of one part in 10,000 are necessary. An accuracy of this magnitude is generally not available through an analog circuit unless highly precise analog components are used. Such components are quite expensive. Second, the analog circuit disclosed in this patent cannot be independently calibrated to compensate for changing characteristics of the electronic components—such as offset, drift, aging and the like. Specifically, this circuit is calibrated on a "lumped" basis, i.e. by first passing a known fluid, such as water, through the meter and then adjusting the circuit to provide the proper density reading at its output. This process compensates for any errors that occur at the time of calibration that are attributable either to physical errors in measuring density using a Coriolis mass flow meter or to errors generated by the changing characteristics of the electrical components themselves. Unfortunately, after the circuit has been calibrated in this fashion, component characteristics will subsequently change over time and thereby inject errors into the density readings produced by the circuit. This, in turn, will eventually necessitate an entire re-calibration.

All densitometers are generally calibrated using a calibration fluid having a known density. This density is specified at a certain temperature. Unfortunately, the density of most fluids varies with temperature; some fluids exhibit a significant variation, while other fluids exhibit relatively little variation. Consequently, many currently available densitometers require that the temperature of the calibration fluid must be carefully controlled before the fluid is injected into the densitometer for calibration. This necessitates that the container holding the fluid must be placed in a temperature bath for a sufficiently long period of time so that the fluid will stabilize to a desired temperature. In addition, provisions must be made to ensure that the temperature of the fluid will not change as the fluid is pumped through the meter. Accurately controlling the temperature of a fluid and then accurately maintaining its temperature, while the fluid is being pumped through the meter, is both a costly and tedious process.

It may be appreciated from the foregoing that a need exists in the art for a high-accuracy densitometer which is capable of operation under the high temperature, pressure, shock and vibration conditions encountered in a wellbore; which uses relatively inexpensive components; which substantially eliminates any error caused by changing characteristics of any of the electronic components; and which effectively eliminates the errors associated with the effects of temperature and pressure on the system.

SUMMARY OF THE INVENTION

Accordingly, there is disclosed herein a measurement device for determining fluid properties from vibration frequencies of a sample cavity and a reference cavity. In one embodiment, the measurement device includes a sample flow tube, a reference flow tube, vibration sources and detectors mounted on the tubes, and a measurement module. The sample flow tube receives a flow of sample fluid for characterization. The reference flow tube is filled with a reference fluid having well-characterized properties. The reference flow tube may be pressure balanced to the same pressure as the sample. The measurement module employs the vibration sources to generate vibrations in both tubes. The measurement module combines the signals from the vibration detectors on the tubes to determine properties of the sample fluid, such as density, viscosity, compressibility, water fraction, and bubble size. The measurement module may further detect certain flow patterns such as slug flow, for example.

To determine the sample fluid density, the measurement module measures the difference between resonance frequencies of the sample flow tube and the reference flow tube. The density can then be calculated according to a formula. Other fluid properties may be determined from the sample tube's resonance peak amplitude, peak width and/or peak shape. Variation of the density measurements may be used to detect and characterize multiple phase fluid flow. The use of a reference tube in the disclosed measurement device is expected to greatly enhance the accuracy and reliability of the measurement device over a range of temperatures, pressures, and shock accelerations such as those that may be found in a borehole.

BRIEF DESCRIPTION OF THE DRAWINGS

A better understanding of the present invention can be obtained when the following detailed description of the preferred embodiment is considered in conjunction with the following drawings, in which.

Figure 1A:
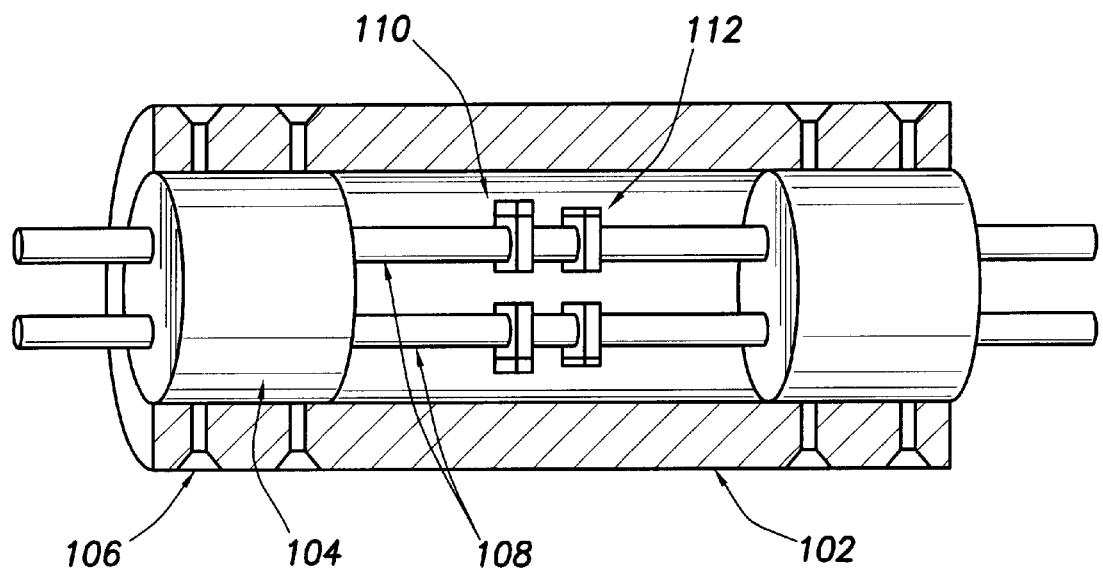
FIG. 1A shows a densitometer according to a preferred embodiment of the present invention.

While the invention is susceptible to various modifications and alternative forms, specific embodiments thereof are shown by way of example in the drawings and will herein be described in detail. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE PREFERRED EMBODIMENT

Referring now to FIG. 1A, one embodiment of a device for measuring density and viscosity of a flowing fluid generally includes a rigid housing 102, two bulkheads 104, fasteners 106, flow tubes 108, vibration sources 110, vibration detectors 112, and a measurement module (not shown). The rigid housing 102 surrounds and protects a volume through which the flow tubes 108 pass and reduces the response to vibrations not associated with particular modes of the flow tubes. The bulkheads 104 seal the volume and secure the flow tubes 108 within that volume. Fasteners 106 are provided to secure the bulkheads 104 to the rigid housing 102. The volume preferably contains air, a vacuum or a relatively inert gas such as nitrogen or argon. If gasses are used, then they are preferably at atmospheric pressure when the device is at room temperature.

Rigid housing 102, bulkheads 104, and flow tubes 108 are preferably made from materials that can withstand pressures of more than 20,000 psi (pounds per square inch) at temperatures of 250° C. or more. Two examples of suitable materials are Titanium and Hastaloy-HA276C. The flow tubes 108 may be welded to the bulkheads 104, or (as discussed further below) mechanically isolated from the bulkheads 104.

The flow tubes 108 are preferably straight, as this reduces any tendencies for plugging and erosion by materials passing through the flow tubes 108. However, it is recognized that bent tubes of various shapes, including "U"-shaped tubes, may provide greater measurement sensitivities.

Contemplated dimensions for the embodiment of FIG. 1A are shown in Table 1:

TABLE 1

|  | Flow Tube | Bulkhead | Housing |
|---|---|---|---|
| Length | 6" | 2" | 10" |
| Outer Diam | 0.304" | 1.5" | 2" |
| Inner Diam | 0.219" | — | ~1.5" |

However, it is noted that other dimensions may be used without departing from the scope of the invention.

Figure 1B:
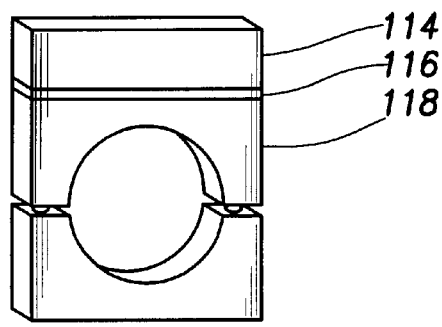
FIG. 1B shows a piezoelectric vibratory source.

The vibration sources 110 are piezoelectric transducers such as those shown in FIG. 1B. They include a clamp 118 for securing the vibration source to the flow tube 108, an inertial or "backing" mass 114, and a piezoelectric layer 116 sandwiched between the clamp 118 and the inertial mass 114. When a voltage is applied to the piezoelectric layer 116, the layer expands, driving the tube 108 and mass 114 away from each other. When the voltage is subsequently removed or reversed, the layer contracts, pulling the tube and the mass together. Application of an oscillating voltage to the piezoelectric layer imparts a vibratory motion to the flow tube.

As discussed farther below, the flow tube 108 has a resonance frequency that depends on the density of the fluid it contains. When the vibration source 110 drives the flow tube 108 at a resonance frequency, the vibration of the tube reaches maximum amplitude (displacement), and the energy required to drive the vibration reaches a local minimum.

The vibration detectors 112 shown in FIG. 1A are piezoelectric devices with a structure similar to the vibration sources 110. A piezoelectric transducer is sandwiched between a clamp and an inertial mass. When the piezoelectric transducer is compressed (e.g. by movement of the clamp toward the inertial mass), it generates a voltage. When the layer is subsequently restored or expanded (e.g. by movement of the clamp away from the inertial mass), the voltage decreases. Vibration of the vibration detector 112 causes the detector to generate an electrical signal that oscillates at the vibration frequency. The amplitude of the electrical signal increases with the amplitude of the vibration.

Figure 4:
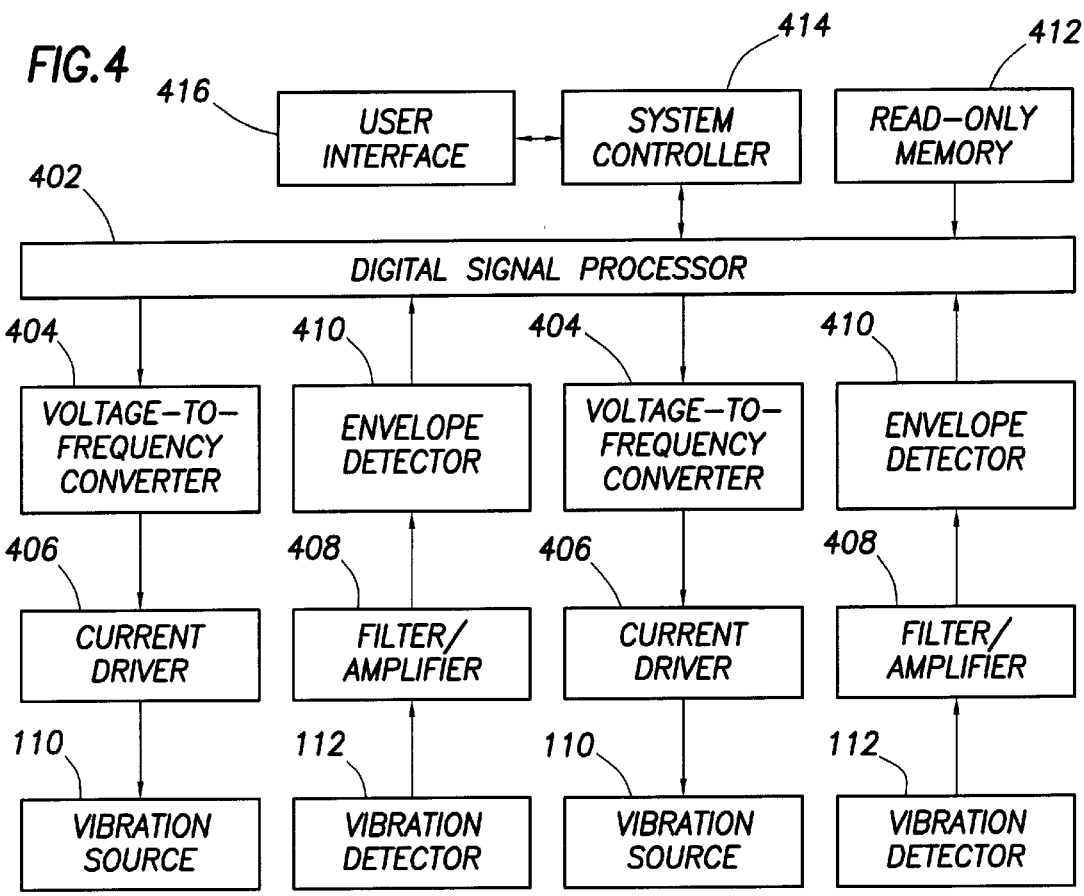
FIG. 4 shows an exemplary measurement module.

Referring now to FIG. 4, one embodiment of the measurement module generally includes a digital signal processor 402, two voltage-to-frequency converters 404, two current drivers 406, two filter/amplifiers 408, two amplitude detectors 410, and a read-only memory (ROM) 412. The digital signal processor 402 may be configured and controlled by a system controller 414 that operates in response to actions of the user on the user interface 416. The system controller 414 preferably also retrieves measurements from the digital signal processor 402 and provides them to the user interface 416 for display to the user.

The digital signal processor 402 preferably executes a set of software instructions stored in ROM 412. Typically, configuration parameters are provided by the software programmer so that some aspects of the digital signal processor's operation can be customized by the user via interface 416 and system controller 414. Preferably, the set of software instructions causes the digital signal processor 402 to perform density measurements according to one or more of the methods detailed further below. The digital signal processor preferably includes digital to analog (D/A) and analog to digital (A/D) conversion circuitry for providing and receiving analog signals to off-chip components. Generally, most on-chip operations by the digital signal processor are performed on digital signals.

In performing one of the methods described further below, the digital signal processor 402 provides a voltage signal to the voltage-to-frequency converter 404. The voltage-to-frequency converter 404 produces a frequency signal having a frequency proportional to the input voltage; The current driver 406 receives this frequency signal and amplifies it to drive the vibration source 110. The vibration source 110 causes the flow tube to vibrate, and the vibrations are detected by vibration detector 112. A filter/amplifier 408 receives the detection signal from vibration detector 112 and provides some filtering and amplification of the detection signal before passing the detection signal to the amplitude detector 410. The filter/amplifier 408 serves to isolate the vibration detector 112 from the amplitude detector 410 to prevent the amplitude detector 410 from electrically loading the vibration detector 112 and thereby adversely affecting the detection sensitivity. The amplitude detector 410 produces a voltage signal indicative of the amplitude of the detection signal. The digital signal processor 402 measures this voltage signal, and is thereby able to determine a vibration amplitude for the chosen vibration frequency.

Figure 3:
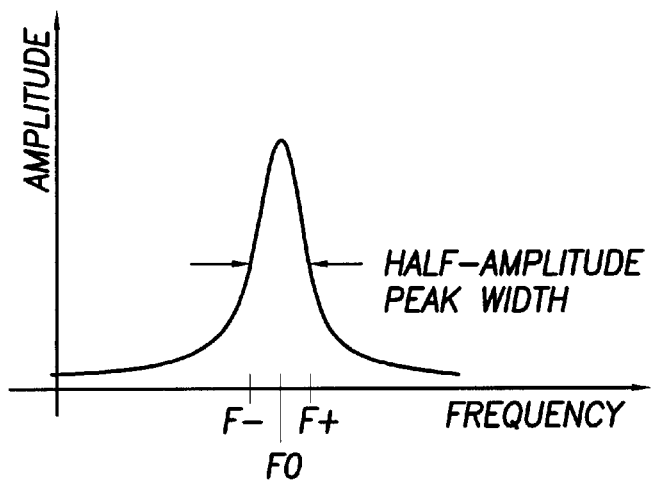
FIG. 3 shows a graph of an exemplary resonance peak.

The measurement module employs the vibration sources 110 and vibration detectors 112 to locate and characterize the resonance frequencies of the flow tubes 108. Several different methods are contemplated. In a first method, the measurement module causes the vibration sources 110 to perform a frequency "sweep" across the range of interest, and records the amplitude readings from the vibration detectors 112 as a function of the frequency. As shown in FIG. 3, a plot of the vibration amplitude versus frequency will show a peak at the resonance frequency $f_0$. The resonance frequency can be converted to a density measurement, and the shape of the peak may yield additional information such as viscosity and multiple phase information.

Figure 5:
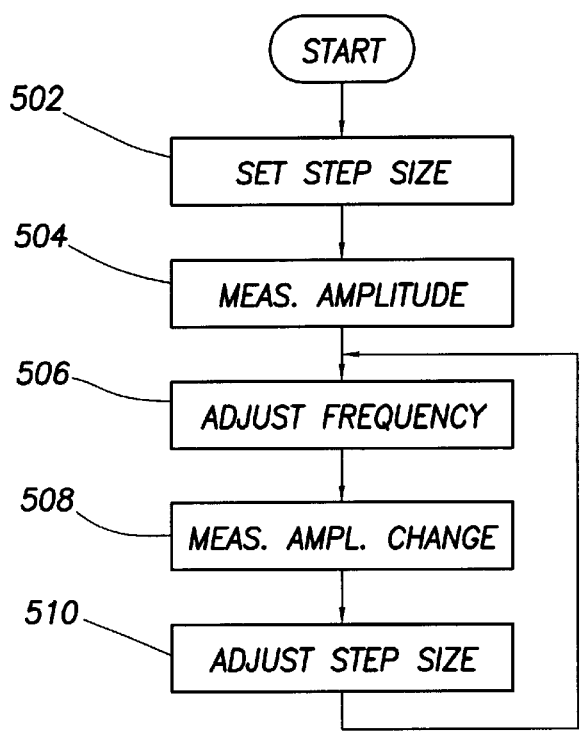
FIG. 5 shows a method for adaptive tracking of a resonance frequency.

In a second method, the measurement module adaptively tracks the resonance frequency using a feedback control technique. One implementation of this method is shown in FIG. 5. An initial step size for changing the frequency is chosen in block 502. This step size can be positive or negative, to respectively increase or decrease the frequency. In block 504, the vibration source is activated and an initial amplitude measurement is made. In block 506, the vibration frequency is adjusted by an amount determined by the step size. In block 508, a measurement of the amplitude at the new frequency is made, and from this, an estimate of the derivative can be made. The derivative may be estimated to be the change in amplitude divided by the change in frequency, but the estimate preferably includes some filtering to reduce the effect of measurement noise. From this estimated derivative, a distance and direction to the resonance peak can be estimated. For example, if the derivative is large and positive, then referring to FIG. 3 it becomes clear that the current frequency is less than the resonance frequency, but the resonance frequency is nearby. For small derivatives, if the sign of the derivative is changing regularly, then the current frequency is very near the resonance frequency. For small negative derivatives without any changes of sign between iterations, the current frequency is much higher than the resonance frequency. Returning to FIG. 5, this information is used to adjust the step size in block 510, and the digital signal processor 402 returns to block 506. This method may work best for providing a fast measurement response to changing fluid densities.

Figure 6:
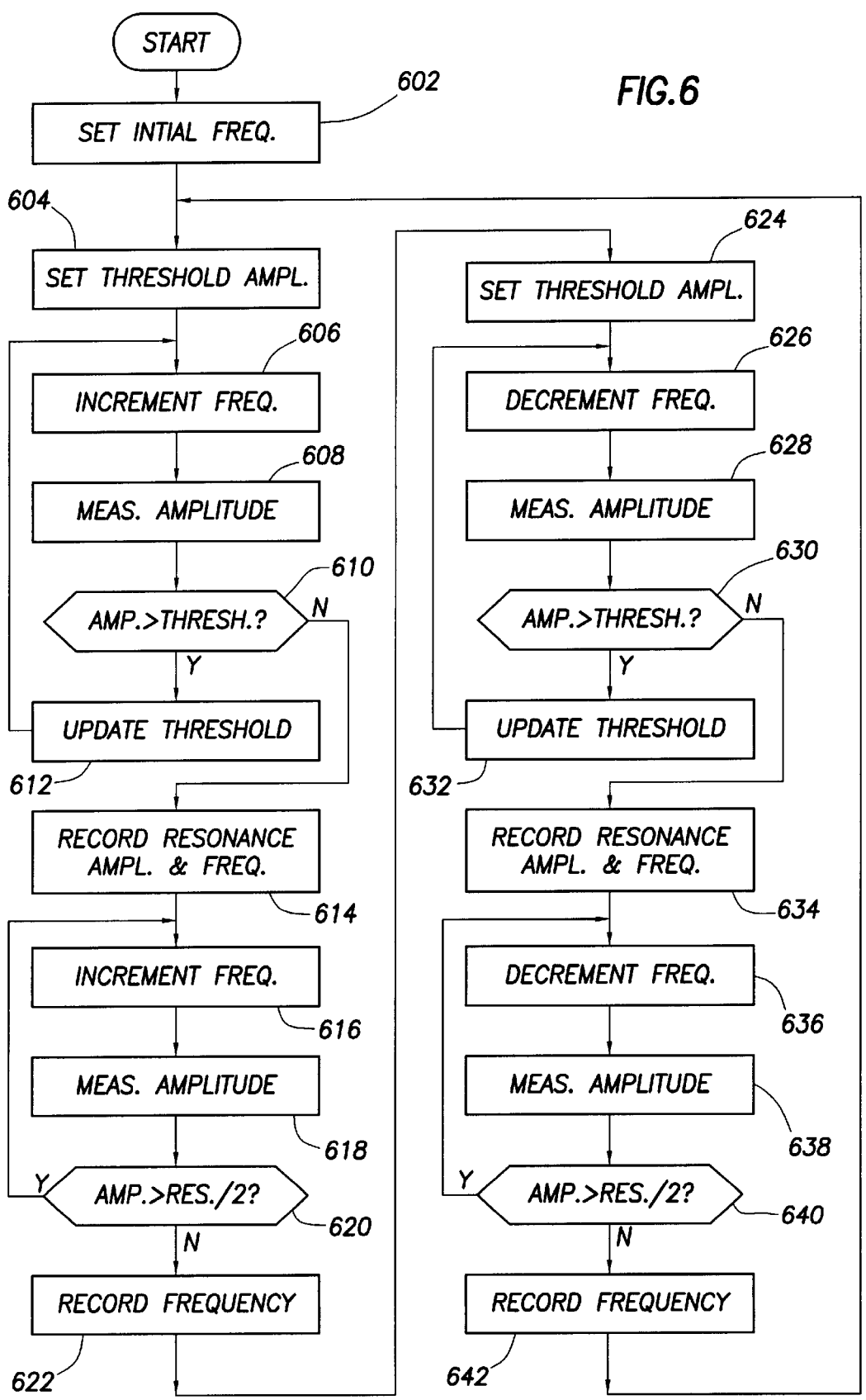
FIG. 6 shows a method for measuring resonance peak frequency, amplitude, and width.

In a third method, the measurement module employs an iterative technique to search for the maximum amplitude as the frequency is discretely varied. Any of the well-known search algorithms for minima or maxima may be used. One illustrative example is now described, but it is recognized that the invention is not limited to the described details. In essence, the exemplary search method uses a back-and-forth search method in which the measurement module sweeps the vibration source frequency from one half-amplitude point across the peak to the other half-amplitude point and back again. One implementation of this method is shown in FIG. 6. In block 602, vibration is induced at an initial (minimum) frequency. In block 604, the vibration amplitude at the current vibration frequency is measured and set as a threshold. In block 606, the frequency is increased by a predetermined amount, and in block 608, the amplitude at the new frequency is measured. Block 610 compares the measured amplitude to the threshold, and if the amplitude is larger, then the threshold is set equal to the measured amplitude in block 612. Blocks 606–612 are repeated until the measured amplitude falls below the threshold. At this point, the threshold indicates the maximum measured amplitude, which occurred at the resonance peak. The amplitude and frequency are recorded in block 614. The frequency increases and amplitude measurements continue in blocks 616 and 618, and block 620 compares the amplitude measurements to half the recorded resonance frequency. Blocks 616–620 are repeated until the amplitude measurement falls below half the resonance peak amplitude, at which point, the half-amplitude frequency is recorded in block 622. Blocks 624–642 duplicate the operations of corresponding blocks 602–622, except that the frequency sweep across the resonance peak occurs in the opposite direction. For each peak crossing, the measurement module records the resonance amplitude and frequency, and then records the subsequent half-amplitude frequency. From this information the peak width and asymmetry can be determined, and the fluid density, viscosity, and multiple phase information can be calculated.

The measurement module is an electronic circuit that may have temperature, pressure, and age-dependent variations. The densitometer structure as a whole may also exhibit these variations. Since it is expected that the densitometer will be exposed to temperature and pressure extremes over the device lifetime, it is unrealistic to believe that the device can sustain a given set of calibration settings. To circumvent the need for frequent re-calibrations, one of the flow tubes 108 is set up as a "vibration standard" that has a well-determined resonance frequency, and the resonance frequency of the other flow tube (hereafter termed the sample flow tube) is measured relative to the standard, or reference, flow tube. The sample flow tube accepts a flow of the sample fluid whose density is to be measured in one end and discharges the flow from the other end.

As the properties of water are extremely well known, it is preferred to have the reference flow tube filled with water. Alternatively, the reference flow tube may be filled with a vacuum, a gas, or some other substance with well known density properties (e.g. a reference solid). For the present purposes, the reference tube is considered to contain a vacuum if at room temperature the internal pressure is less than 0.05 atmospheres. Any fluid in the reference flow tube is preferably subjected to the pressure and temperature of the sample fluid's environment. Thermometers and pressure meters are preferably provided to determine what these temperature and pressure values are.

The measurement module preferably employs one vibration source 110 and one vibration detector 112 to adaptively track the resonance frequency of the reference flow tube 108. The measurement module then measures the frequency of the vibration signal from the sample tube relative to the resonance frequency signal from the reference tube. In one embodiment, the measurement module adds the two signals to obtain a signal that exhibits a beat frequency. The frequency of the beats is equal to the (unsigned) difference between the resonance frequency and the frequency of the vibration signal. The sign of the difference can be determined in a number of ways. One method is to utilize a fluid in the reference tube that is outside the anticipated density range (either lighter or heavier) of the sample. A second, different, reference tube could be used to determine a second beat frequency. Another method is to de-tune the frequency of the sample tube from its resonant frequency and observe the change in the measured frequency difference. For example, if an increase in the driving frequency results in an increase of the frequency difference, the resonant frequency of the sample is greater than that of the reference. Alternatively, the drive frequency of the reference tube could be de-tuned with similar results. From the signed difference, the density of the unknown fluid can be determined. A method for determining the density of the unknown fluid is presented further below.

Figure 2:
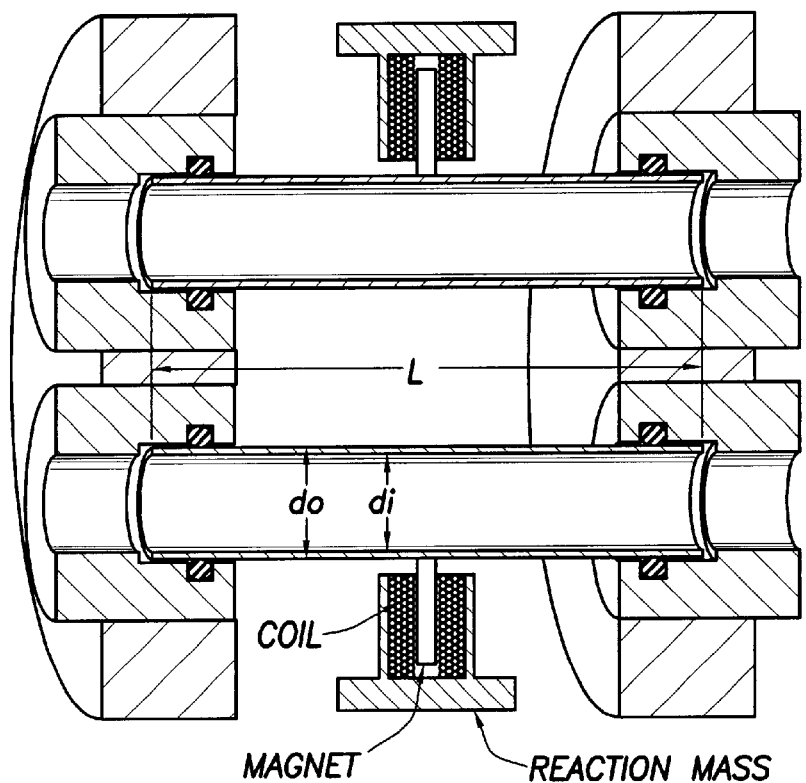
FIG. 2 shows an alternative embodiment of a densitometer according to the present invention.

Turning now to FIG. 2, a second embodiment is shown. In FIG. 2, the flow tubes are mechanically isolated from the mounting structure by elastomeric seals 202. This makes the ends free to vibrate because the seals are soft and the deflections are small, but perhaps more significantly, this configuration may eliminate most of the extraneous vibration noise from the flow tubes. The vibration sources shown for this embodiment are inductive coils 204. Electrical currents passing through the inductive coils generate a magnetic field that attracts or repels a permanent magnet. By alternating the current direction at a desired vibration frequency, the magnet can be forced to vibrate the flow tubes at that frequency.

The position of the magnet can be measured from the back EMF (electromotive force) that the coil generates, so the inductive coils can also be used as the vibration sensors. Alternatively, a separate inductive coil may serve as a vibration sensor, as may any one of a multitude of other position sensors including piezoelectric devices, Hall-effect sensors, interferometers, strain gauges, capacitance meters, accelerometers, etc.

It is noted that in both embodiments, the vibration sources and vibration detectors are preferably mounted near an antinode (point of maximum displacement from the equilibrium position) of the mode of vibration they are intended to excite and monitor. It is contemplated that more than one mode of vibration may be employed (e.g. the vibration source may switch between multiple frequencies to obtain information from higher resonance harmonic frequencies). The vibration sources and detectors are preferably positioned so as to be near antinodes for each of the vibration modes of interest.

The locations of nodes (points of zero vibrational amplitude) and antinodes are determined by the wavelength of the vibration mode. The frequency f and wavelength $\lambda$ are related to the speed of sound v in the material by the equation $v=f\lambda$.

The following notation is used for the resonance frequency derivation:

A vibration system constant (22.4 fixed ends, 22.4 free ends, 3.52 cantilevered on one end)
A calibration constant (lbf/(in$^3$-sec$^2$)
B calibration constant (lbf/(in$^3$)
$f_n$ natural frequency (Hz)
p period of natural frequency (sec)
$\rho$ fluid density (lbf/in$^3$)
$\rho_t$ tube material density (lbf/in$^3$)
$\mu$ system mass per unit length (lbf-sec$^2$/in$^2$)
$\mu_f$ fluid mass per unit length (lbf-sec$^2$/in$^2$)
$\mu_t$ tube mass per unit length (lbf-sec$^2$/in$^2$)
$d_o$ tube outside diameter (in)
$d_i$ tube inside diameter (in)
l tube length (in)
E tube modulus of elasticity (psi)
I area moment of inertia of the tube cross section (in$_4$)
g gravitational constant (386.4 in/sec$^2$)
The natural frequency of the tube can be calculated as follows (see page 1–14 of the Shock and Vibration Handbook, McGraw Hill, N.Y., 1976.):

$$f_n = \frac{A}{2\pi}\sqrt{\frac{E \cdot I}{\mu \cdot l^4}} \text{ (Hz)} \quad (1)$$

A is determined by the geometry of the system, and is 22.4 for the first mode of vibration in a tube with fixed ends or free ends. The area moment of inertia of a tube (I) is given by:

$$I = \frac{\pi d_o^4}{64}\left(1 - \frac{d_i^4}{d_o^4}\right)(\text{in}^4) \quad (2)$$

The mass per unit length $\mu$ consists of the tube's weight and the fluid's weight divided by the length of the tube and the gravitational constant (g=386.4 in/ sec$^2$):

$$\mu_t = \frac{\rho_t \pi}{g}\frac{(d_o^2 - d_i^2)}{4}(\text{lbf-sec}^2/\text{in}^2) \quad (3)$$

$$\mu_f = \frac{\rho \pi}{g}\frac{d_i^2}{4}(\text{lbf-sec}^2/\text{in}^2) \quad (4)$$

$$\mu = \mu_t + \mu_f = \frac{\rho_t d_o^2 \pi}{g4}\left(1 - \frac{d_i^2}{d_o^2}\left(1 - \frac{\rho}{\rho_t}\right)\right)(\text{lbf-sec}^2/\text{in}^2) \quad (5)$$

Substituting Equations 2 and 5 into Equation 1 yields an estimate of the natural frequency:

$$f_n = \frac{A}{2\pi}\sqrt{\frac{E \cdot \frac{\pi d_o^4}{64}\left(1 - \frac{d_i^4}{d_o^4}\right)}{\frac{\rho_t d_o^2 \pi}{g4}\left(1 - \frac{d_i^2}{d_o^2}\left(1 - \frac{\rho}{\rho_t}\right)\right) \cdot l^4}} = \frac{Ad_o}{8\pi l^2}\sqrt{\frac{Eg\left(1 - \frac{d_i^4}{d_o^4}\right)}{\rho_t\left(1 - \frac{d_i^2}{d_o^2}\left(1 - \frac{\rho}{\rho_t}\right)\right)}} \text{ (Hz)} \quad (6)$$

Solving Equation 6 for density yields:

$$\rho = Eg\left(\frac{Ad_o^2}{f_n 8\pi d_i l^2}\right)^2\left(1 - \frac{d_i^4}{d_o^4}\right) - \rho_t\left(\frac{d_o^2}{d_i^2} - 1\right) \quad (7)$$

Equation 7 can be expressed in terms of constant coefficients A & B:

TABLE 2

| | Hastaloy-HA276C | | | Titanium | | |
|---|---|---|---|---|---|---|
| | Cantilever | Fixed | Fixed | Cantilever | Fixed | Fixed |
| Variables: | | | | | | |
| A | 3.52 | 22.4 | 22.4 | 3.52 | 22.4 | 22.4 |
| E | 29.8 10⁶ | 29.8 10⁶ | 29.8 10⁶ | 15.0 10⁶ | 15.0 10⁶ | 15.0 10⁶ |
| g | 386.4 | 386.4 | 386.4 | 386.4 | 386.4 | 386.4 |
| di | 0.09 | 0.219 | 0.219 | 0.09 | 0.219 | 0.219 |
| do | 0.125 | 0.304 | 0.304 | 0.125 | 0.304 | 0.304 |
| σ stress | 63056.48 | 63154.651 | 63154.651 | 63056.478 | 63154.651 | 63154.651 |
| l | 4 | 16 | 6 | 4 | 16 | 6 |
| ρ$^t$ | 0.321 | 0.321 | 0.321 | 0.175 | 0.175 | 0.175 |
| ρ$^{-sg}$ = 1 | 0.0361 | | | 0.0361 | | |
| Results: | | | | | | |
| ρ$^{-sg}$ | fn | fn | fn | fn | fn | fn |
| 2 | 229.13 | 221.62 | 1575.98 | 204.19 | 197.47 | 1404.26 |
| 1.8 | 231.40 | 223.82 | 1591.60 | 207.40 | 200.59 | 1426.40 |
| 1.6 | 233.73 | 226.08 | 1607.69 | 210.77 | 203.85 | 1449.62 |
| 1.4 | 236.14 | 228.41 | 1624.28 | 214.31 | 207.28 | 1474.02 |
| 1.2 | 238.62 | 230.82 | 1641.39 | 218.04 | 210.89 | 1499.68 |
| 1 | 241.18 | 233.30 | 1659.06 | 221.97 | 214.70 | 1526.74 |
| 0.8 | 243.83 | 235.87 | 1677.30 | 226.11 | 218.72 | 1555.31 |
| 0.6 | 246.57 | 238.52 | 1696.17 | 230.50 | 222.97 | 1585.56 |
| 0.4 | 249.40 | 241.27 | 1715.68 | 235.15 | 227.48 | 1617.63 |
| 0.2 | 252.33 | 244.11 | 1735.89 | 240.10 | 232.28 | 1651.74 |
| 0.00122 | 255.35 | 247.03 | 1756.69 | 245.34 | 237.36 | 1687.87 |
| Δf | 26.22 | 25.41 | 180.71 | 41.15 | 39.88 | 283.61 |
| Δf/f$_c$ | 10.87% | 10.89% | 10.89% | 18.54% | 18.58% | 18.58% |

$$\rho = A/f_n^2 - B \quad (8)$$

Where the coefficients A & B are determined by the tube's material properties and geometry:

$$A = E\left(\frac{gAd_o^2}{8\pi d_i l^2}\right)^2\left(1 - \frac{d_i^4}{d_o^4}\right) \quad (9)$$

$$B = \rho_t\left(\frac{d_o^2}{d_i^2} - 1\right) \quad (10)$$

In practice, the constants A & B may be estimated by fitting a calibration curve.

Table 2 is an example calculation of the natural frequencies for various configurations and materials. The frequencies are calculated as a function of fluid specific gravity (ρ-sg) in a range from near 0 (air) to 2 (heavy mud). The sensitivity of the device can be defined as the change in frequency from air to a heavy mud divided by a center frequency determined with water (specific gravity=1) in the tube. The cantilever device has a sensitivity of 10.87% and the 16" fixed-end straight tube has a sensitivity slightly larger with 10.89%. A 6" fixed-end straight tube exhibits an increased frequency with water (sg=1) to 1659 Hz. It is noted that while the frequency increased, the sensitivity remained unchanged (10.89%). The sensitivity ratios can be increased to 19% by using Titanium, due to its improved stiffness to weight ratio. The housing, when made of steel, exhibits a much higher natural frequency than the tubes (5960 Hz). Hence, it does not couple with the tube modes.

The overriding natural frequency of the tubes is dominated by the tube material and its properties. It is noted that the tube's length has the most significant influence on the natural frequency. The resolution (sensitivity) of the gauge may be increased in terms of frequency change versus density by reducing the weight or density of the tube.

Using Equation 8, $\rho_s$ (the density of the sample fluid in the sample tube) can be expressed in terms of $\rho_r$ (the density of the reference fluid in the reference tube) and Δf (the measured difference in frequencies):

$$\rho_s = \frac{A}{\left(\sqrt{\frac{A}{\rho_R + B}} + \Delta f\right)^2} - B \quad (11)$$

It is expected that the accuracy of this calculation may be limited by the calibration accuracy for A and B and the frequency resolution.

Figure 7:
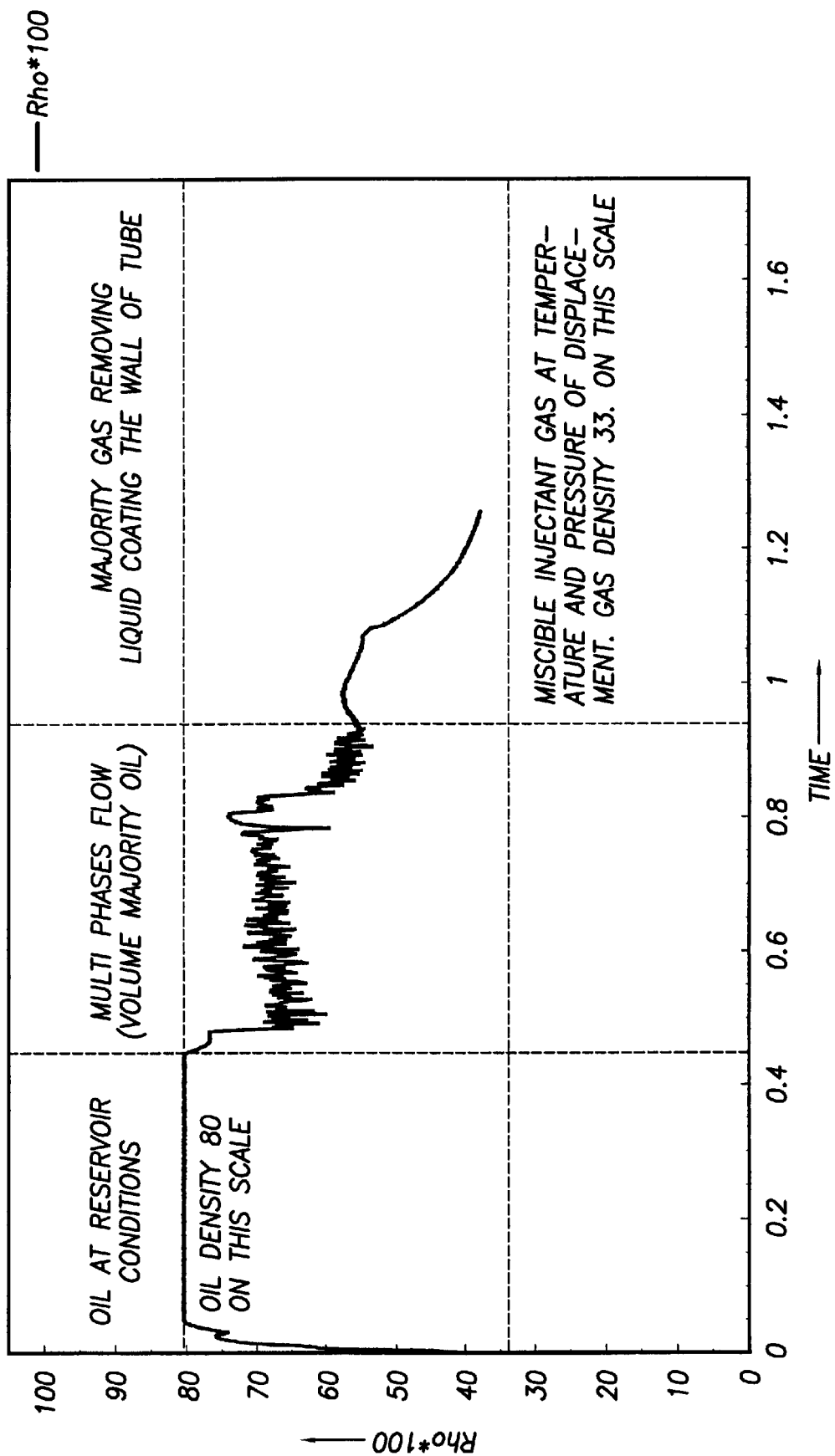
FIG. 7 shows a graph of a measured density as a function of time.

FIG. 7 shows an example of density measurements made according to the disclosed method as a function of time. Initially, the sample flow tube fills with oil, and the density measurement quickly converges to a specific gravity of 0.80. As a miscible gas is injected into the flow stream, the sample tube receives a multiple-phase flow stream, and the density measurement exhibits a significant measurement variation. As the flow stream becomes mostly gas, the oil forms a gradually thinning coating on the wall of the tube, and the density measurement converges smoothly to 0.33. It is noted that in the multiple-phase flow region, the density measurement exhibits a variance that may be used to detect the presence of multiple phases.

Air or gas present in the flowing fluid affect the densitometer measurements. Gas that is well-mixed or entrained in the liquid may simply require slightly more drive power to keep the tube vibrating. Gas that breaks out, forming voids in the liquid, will reduce the amplitude of the vibrations due to damping of the vibrating tube. Small void fractions will cause variations in signals due to local variation in the system density, and power dissipation in the fluid. The result is a variable signal whose envelope corresponds to the densities of the individual phases. In energy-limited systems, larger void fractions can cause the tube to stop vibrating altogether when the energy absorbed by the fluid exceeds that available. Nonetheless, slug flow conditions can be detected by the flowmeter electronics in many cases, because they manifest themselves as periodic changes in measurement characteristics such as drive power, measured density, or amplitude. Because of the ability to detect bubbles, the disclosed densitometer can be used to determine the bubble-point pressure. As the pressure on the sample fluid is varied, bubbles will form at the bubble point pressure and will be detected by the disclosed device.

If a sample is flowing through the tube continuously during a downhole sampling event, the fluids will change from borehole mud, to mud filtrate and cake fragments, to majority filtrate, and then to reservoir fluids (gas, oil or water). When distinct multiple phases flow through the tube, the sensor output will oscillate within a range bounded by the individual phase densities. If the system is finely homogenized, the reported density will approach the bulk density of the fluid. To enhance the detection of bulk fluid densities, the disclosed measurement devices may be configured to use higher flow rates through the tube to achieve a more statistically significant sample density. Thus, the flow rate of the sample through the device can be regulated to enhance detection of multiple phases (by decreasing the flow rate) or to enhance bulk density determinations (by increasing the flow rate). If the flow conditions are manipulated to allow phase settling and agglomeration (intermittent flow or slipstream flow with low flow rates), then the vibrating tube system can be configured to accurately detect multiple phases at various pressures and temperatures. The fluid sample may be held stagnant in the sample chamber or may be flowed through the sample chamber.

In addition, the resonance frequency (or frequency difference) may be combined with the measured amplitude of the vibration signal to calculate the sample fluid viscosity. The density and a second fluid property (e.g. the viscosity) may also be calculated from the resonance frequency and one or both of the half-amplitude frequencies. Finally, vibration frequency of the sample tube can be varied to determine the peak shape of the sample tube's frequency response, and the peak shape used to determine sample fluid properties.

The disclosed instrument can be configured to detect fluid types (e.g. fluids may be characterized by density), multiple phases, phase changes and additional fluid properties such as viscosity and compressibility. The tube can be configured to be highly sensitive to changes in sample density and phases. For example, the flow tubes may be formed into any of a variety of bent configurations that provide greater displacements and frequency sensitivities. Other excitation sources may be used. Rather than using a variable frequency vibration source, the tubes may be knocked or jarred to cause a vibration. The frequencies and envelope of the decaying vibration will yield similar fluid information and may provide additional information relative to the currently preferred variable frequency vibration source.

The disclosed devices can quickly and accurately provide measurements of downhole density and pressure gradients. The gradient information is expected to be valuable in determining reservoir conditions at locations away from the immediate vicinity of the borehole. In particular, the gradient information may provide identification of fluids contained in the reservoir and the location(s) of fluid contacts. Table 3 shows exemplary gradients that result from reservoir fluids in a formation.

Determination fluid contacts(Gas/Oil and Oil/Water) is of primary importance in reservoir engineering. A continuous vertical column may contain zones of gas, oil and water, Current methods require repeated sampling of reservoir pressures as a function of true vertical depth in order to calculate the pressure gradient (usually psi/ft) in each zone. A fluid contact is indicated by the intersection of gradients from two adjacent zones (as a function of depth). Traditionally, two or more samples within a zone are required to define the pressure gradient.

The pressure gradient ($\Delta p/\Delta h$) is related to the density of the fluid in a particular zone. This follows from the expression for the pressure exerted by a hydrostatic column of height h.

$$P = \rho * g * h \tag{12}$$

TABLE 3

| Fluid | Density Gm/cc | Gradient psi/ft |
|---|---|---|
| Low Pressure Gas Cap | 0.10 | 0.04 |
| Gas Condensate | 0.20 | 0.09 |
| Light Oil | 0.50 | 0.22 |
| Med. Oil | 0.70 | 0.30 |
| Heavy Oil | 0.90 | 0.39 |
| Pure Water | 1.00 | 0.43 |
| Formation Water | ≧1.00 | ≧0.43 |
| Mud Filtrate (from 8.7 ppg) | 1.04 | 0.45 |
| Completion Brine | 1.08 | 0.47 |
| Mud (12.5 ppg) | 1.50 | 0.65 | where P denotes pressure, $\rho$ denotes density, g denotes gravitational acceleration, and h denotes elevation.

In a particular zone, with overburden pressure which differs from that of a continuous fluid column, the density of the fluid may be determined by measuring the pressure at two or more depths in the zone, and calculating the pressure gradient:

$$\rho = \frac{\Delta P / \Delta h}{g} \tag{13}$$

However, the downhole densitometer directly determines the density of the fluid. This allows contact estimation with only one sample point per zone. If multiple samples are acquired within a zone, the data quality is improved. The gradient determination can then be cross-checked for errors which may occur. A high degree of confidence is achieved when both the densitometer and the classically determined gradient agree.

Once the gradient for each fluid zone has been determined, the gradient intersections of adjacent zones are determined. The contact depth is calculated as the gradient intersection at true vertical depth.

Numerous variations and modifications will become apparent to those skilled in the art once the above disclosure is fully appreciated. For example, the flow tubes may be replaced with sample chambers of any rigid variety. It is intended that the following claims be interpreted to embrace all such variations and modifications.

It is noted that when the disclosed device uses a reference fluid in the reference tube, the reference fluid is preferably subjected to substantially the same pressure and temperature as the sample fluid. When the reference tube has an excitation source mounted on the tube to generate vibration of the reference tube, the vibration of the reference tube may also induce vibration of the sample tube.

What is claimed is:

1. A device for determining a property of a sample fluid, wherein the device comprises:
   a sample tube having a bore that receives a fluid sample, wherein the tube vibrates at a frequency characteristic of one or more properties of the fluid sample;
   a vibration sensor that converts vibrations of the sample tube into a measurement signal;
   a reference standard that provides a reference frequency signal; and
   a measurement module that receives the measurement signal and the reference frequency signal, and that determines a beat frequency of the measurement and reference signals to determine a property of the sample fluid.

2. The device of claim 1, wherein the fluid sample includes a liquid.

3. The device of claim 1, wherein the fluid sample includes a gas.

4. The device of claim 1, wherein the fluid sample includes suspended solids.

5. The device of claim 1, wherein the reference standard includes a solid cylinder having a length and diameter equal to those of the sample tube.

6. The device of claim 1, wherein the vibration sensor is mechanically coupled to the sample tube.

7. The device of claim 1, wherein the vibration sensor is further configured to generate vibration of the sample tube.

8. The device of claim 1, wherein multiple vibration sensors are coupled to the sample tube.

9. The device of claim 1, wherein the measurement module is configured to determine the vibration frequency response of the sample tube.

10. The device of claim 1, wherein the measurement module is configured to determine the vibration amplitude of the sample tube.

11. The device of claim 1, wherein the property of the sample fluid is density.

12. The device of claim 1, wherein the property of the ample fluid is viscosity.

13. The device of claim 1, wherein the property of the sample fluid is bubble point.

14. The device of claim 1, wherein the property of the sample fluid is thermodynamic phase.

15. The device of claim 1, wherein the reference standard includes a reference tube having a bore.

16. The device of claim 15, wherein the bore of the reference tube contains a vacuum.

17. The device of claim 15, wherein the bore of the reference tube contains a reference solid.

18. The device of claim 15, further comprising:
    a second reference tube having a bore having contents different from the first reference tube, wherein the second reference tube is configured to provide a second reference signal to the measurement module.

19. The device of claim 15, further comprising:
    an excitation source mounted on the reference tube to generate vibration of the reference tube, wherein vibration of the reference tube also induces vibration of the sample tube.

20. The device of claim 15, wherein the bore of the reference tube contains a reference fluid.

21. The device of claim 20, wherein the reference fluid is a gas.

22. The device of claim 20, wherein the reference fluid is subjected to substantially the same pressure and temperature as the sample fluid.

23. The device of claim 1, wherein the vibration sensor is an electromechanical sensor.

24. The device of claim 23, wherein the vibration sensor includes a piezoelectric transducer.

25. The device of claim 23, wherein the vibration sensor includes an induction coil.

26. The device of claim 1, further comprising:
    an excitation source configured to generate vibration of the sample tube.

27. The device of claim 26, wherein the excitation source includes a piezoelectric transducer.

28. The device of claim 26, wherein the excitation source includes a magnetorestrictive transducer.

29. The device of claim 26, wherein the excitation source includes an induction coil.

30. The device of claim 26, wherein the excitation source includes a mechanical striker.

31. The device of claim 26, wherein the excitation source is driven by an impulse.

32. The device of claim 26, wherein the excitation source is frequency-swept.

33. The device of claim 26, wherein the excitation source is driven by a phase-lock loop.

34. The device of claim 26, wherein multiple excitation sources are coupled to the sample tube.

35. The device of claim 26, wherein the measurement module is configured to determine the drive power of the excitation source.

36. A method for measuring a property of a fluid, where the method comprises:
    receiving a sample fluid into a sample cavity;
    vibrating the sample cavity to obtain a vibration signal having a sample cavity vibration frequency;
    producing a resonant signal from a vibratory standard independent of the sample cavity, wherein the resonant signal has a resonant frequency;
    determining a frequency difference between the resonant frequency and the sample cavity vibration frequency; and
    converting the frequency difference in to a density measurement of the sample fluid,
    wherein the determining a frequency difference includes:
      combining the vibration signal with the resonant signal to produce a beat-frequency signal; and
      measuring a beat-frequency in the beat-frequency signal.

37. The method of claim 36, further comprising:
    adjusting the sample cavity vibration frequency to determine the frequency differences for a sample cavity resonance frequency and at least one sample cavity half-amplitude frequency; and calculating the density and a second fluid property from the resonance frequency difference and the half-amplitude frequency difference.

38. A method for measuring a property of a fluid, where the method comprises:

receiving a sample fluid into a sample cavity;

vibrating the sample cavity to obtain a vibration signal having a sample cavity vibration frequency;

producing a resonant signal from a vibratory standard independent of the sample cavity, wherein the resonant signal has a resonant frequency;

determining a frequency difference between the resonant frequency and the sample cavity vibration frequency;

varying the sample cavity vibration frequency to determine a sample cavity resonance peak shape; and determining fluid properties from the peak shape.

* * * * *